US009164074B2

(12) United States Patent
Lin

(10) Patent No.: US 9,164,074 B2
(45) Date of Patent: Oct. 20, 2015

(54) FIBRE CLOTH INSPECTING METHOD

(71) Applicant: TAIWAN POWER TESTING TECHNOLOGY CO., LTD., New Taipei (TW)

(72) Inventor: Yu-Chiang Lin, New Taipei (TW)

(73) Assignee: TAIWAN POWER TESTING TECHNOLOGY CO., LTD., New Taipei (TW)

( * ) Notice: Subject to any disclaimer, the term of this patent is extended or adjusted under 35 U.S.C. 154(b) by 284 days.

(21) Appl. No.: 13/730,542

(22) Filed: Dec. 28, 2012

(65) Prior Publication Data

US 2014/0123749 A1 May 8, 2014

(30) Foreign Application Priority Data

Nov. 5, 2012 (TW) .............................. 101141063 A

(51) Int. Cl.
*G01N 33/36* (2006.01)
*G01N 21/898* (2006.01)

(52) U.S. Cl.
CPC .......... *G01N 33/367* (2013.01); *G01N 21/8983* (2013.01)

(58) Field of Classification Search
None
See application file for complete search history.

(56) References Cited

U.S. PATENT DOCUMENTS 4,057,351 A * 11/1977 Fomenko ...................... 356/431
4,070,114 A * 1/1978 Fomenko ...................... 356/521
4,124,300 A * 11/1978 Mead et al. .................. 356/429
4,853,776 A * 8/1989 Itaya et al. ...................... 348/88
5,742,398 A * 4/1998 Laucournet .................. 356/429
5,825,501 A * 10/1998 Mee et al. ...................... 356/429
7,189,959 B1 * 3/2007 Morison et al. .......... 250/227.14

FOREIGN PATENT DOCUMENTS

BE 902741 A * 12/1985

* cited by examiner

*Primary Examiner* — Andre Allen

(74) *Attorney, Agent, or Firm* — Muncy, Geissler, Olds & Lowe, P.C.

(57) ABSTRACT

The invention provides a fiber cloth inspecting method for inspecting a fiber cloth regarding sparse density, filament break, various kinds of mark, fabric runs, break, weaving validation, and dyeing uniformity. The method includes following steps: scanning the fiber cloth by a scanning light beam; retrieving a light pattern generated by the scanning; generating an inspecting result information according to the light pattern in relation to the fiber cloth; and analyzing the fiber cloth regarding sparse density, filament break, various kinds of mark, fabric runs, break, weaving validation, and dyeing uniformity according to the inspecting result information.

6 Claims, 6 Drawing Sheets

FIBRE CLOTH INSPECTING METHOD

FIELD OF THE INVENTION

The present invention relates to a fibre cloth inspecting method, and more particularly to a fibre cloth inspecting method for inspecting a fibre cloth regarding sparse density, filament break, various kinds of mark, fabric runs, break, weaving validation, and dyeing uniformity.

BACKGROUND OF THE INVENTION

Fibre cloth is widely used in modern life. The fibre cloth is applied to various objects, such as clothes, a cover of equipment shell, and architectural materials. And the quality of these objects is relative to the property of the fibre cloth, such as the strength and the stiffness of the fibre cloth. In view of this, the inspection of fibre cloth is therefor so important in order to choose the fibre cloth with good quality.

Traditional fibre cloth inspecting method includes tensile strength testing, tensile rigidity testing, tensile elastic testing, flexural strength testing, and deformation testing, etc. Since these traditional methods could not be processed without destroying the material of fibre cloth itself, it thus leads to the fact that it only allows a portion of fibre cloth to be tested rather than the whole fibre cloth to be test, and that portion of fibre cloth should not be a portion of fibre cloth that is to be processed in the following procedures. Moreover, the result of these traditional methods can only be taken as a reference report while producing real product of fibre cloth. In addition, in the process that fibre is manufactured to become fibre cloth, the process will affect the quality of the fibre cloth, so the reference report generated by the above traditional methods is rather doubtful.

SUMMARY OF THE INVENTION

Since manufacturing process is much relating to the characteristic of fibre cloth including the sparse density, filament break, various kinds of mark, fabric runs, break, weaving validation, and dyeing uniformity, it thus that the testing result generated by using the traditional methods prior to the manufacture of fibre cloth can not be taken as an evaluation of manufactured products.

Accordingly, an aspect of the present invention is to provide a fibre cloth inspecting method for inspecting the sparse density, filament break, various kinds of mark, fabric runs, break, weaving validation, and dyeing uniformity of the fibre cloth under which it solves the problems about evaluation shortage.

The fibre cloth inspecting method comprises following steps: (a) scanning the fibre cloth by a scanning light beam; (b) retrieving a light pattern generated by the scanning; (c) generating an inspecting result information according to the light pattern in relation to the fibre cloth; and (d) analyzing the fibre cloth regarding sparse density, filament break, various kinds of mark, fabric runs, break, weaving validation, and dyeing uniformity according to the inspecting result information.

According to an embodiment of the present invention, in the step (a), the light pattern is generated by having the scanning light beam projecting through the fibre cloth.

According to an embodiment of the present invention, in the step (a), the light pattern is generated by having the scanning light beam reflecting from the fibre cloth.

According to an embodiment of the present invention, in the step (a), the fibre cloth is shifted along a guiding path to pass through a projecting area projected by the scanning light beam.

According to an embodiment of the present invention, in the step (c), a positional mapping relation between the light pattern and the fibre cloth is determined according to the position of the fibre cloth relative to the guiding path.

According to an embodiment of the present invention, in the step (d), the sparse density, the filament break, the various kinds of mark, the fabric runs, the break, the weaving validation, and the dyeing uniformity of the fibre cloth is analyzed according to the magnitude and the color level of the light pattern.

According to an embodiment of the present invention, it further comprises, after step (d), a step of determining the fibre cloth as a defective product while a quality of fibre cloth regarding sparse density, filament break, various kinds mark, fabric runs, break, weaving validation, and dyeing uniformity of the fibre cloth exceeds a predetermined level.

According to an embodiment of the present invention, it further comprises, after step (d), a step of processing the inspecting result information to obtain an inspecting map.

According to an embodiment of the present invention, it further comprises, after step (d), a step of marking a problem area on the inspecting map according to a quality of the fibre cloth regarding sparse density, filament break, various kinds of mark, fabric runs, break, weaving validation, and dyeing uniformity of the fibre cloth.

According to an embodiment of the present invention, in the step (a), the fibre cloth is guided and pulled by a pulling means to pass through a projecting area projected by the scanning light beam, and in the step (c), a positional mapping relation between the light pattern and the fibre cloth is determined according to a pulling speed of the pulling means.

By means of technical means of the present invention, by the scanning light beam, various light patterns relative to various fibre clothes regarding sparse density, filament break, various kinds of mark, fabric runs, break, weaving method, and dyeing uniformity are generated, so as to inspect the sparse density, the filament break, the various kinds of mark, the fabric runs, the break, the weaving validation, and dyeing uniformity of a fibre cloth. And by a further detail inspection and a relational mapping, the size, the quantity, and the position of certain part, such as the fabric runs part, can be known. Thereby, the manufactured product of the fibre cloth can be inspected in a nondestructive manner. And the accuracy of the fibre cloth inspection is increasing so that the manufacturing yield of the fibre cloth can be further raised.

BRIEF DESCRIPTION OF THE DRAWINGS

The structure and the technical means adopted by the present invention to achieve the above and other objects can be best understood by referring to the following detailed description of the preferred embodiments and the accompanying drawings.

DETAILED DESCRIPTION OF THE PREFERRED EMBODIMENTS

The embodiments of the fibre inspecting method are described as follows.

The First Embodiment

Figure 1:
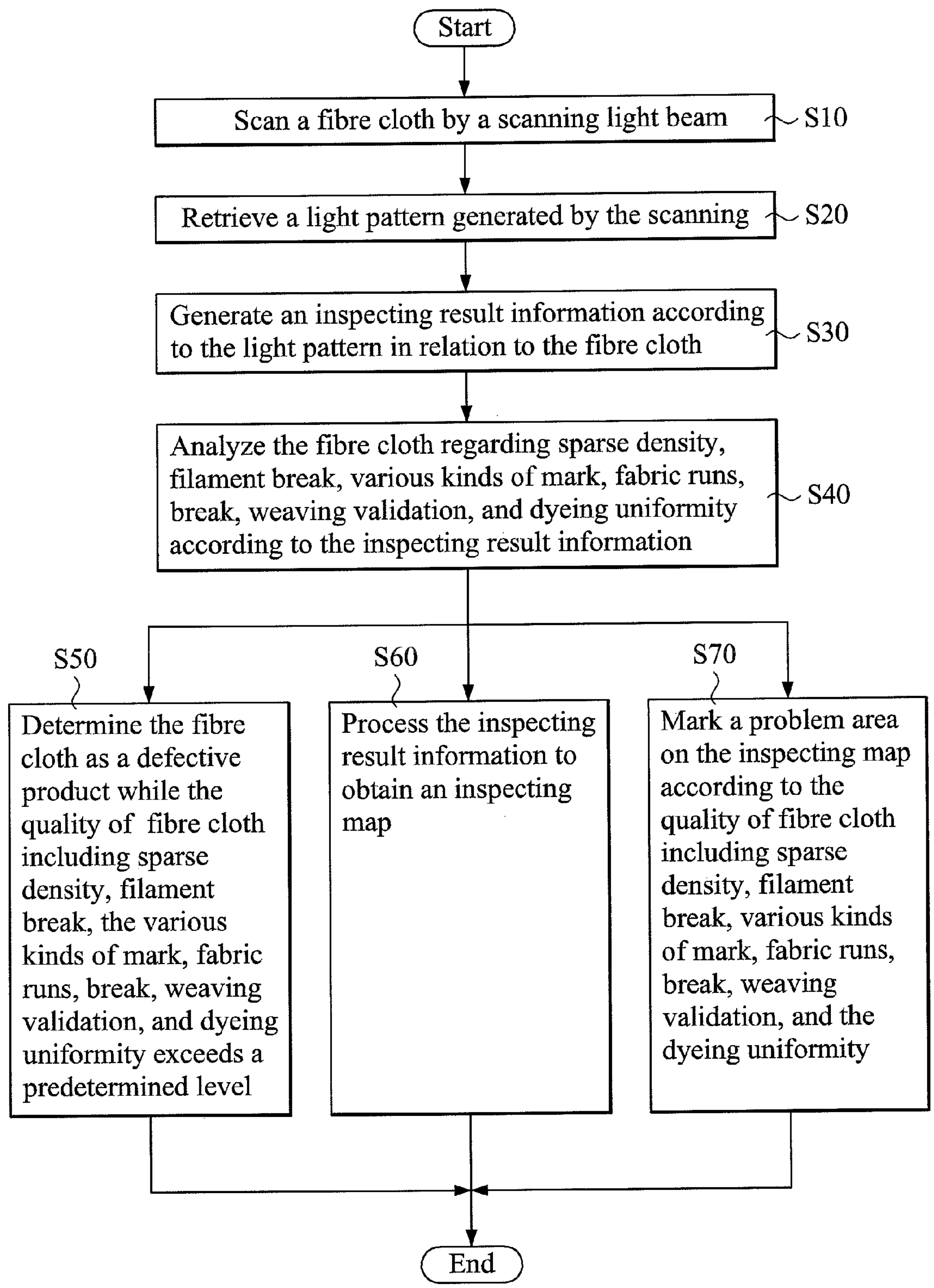
FIG. 1 is a flowchart illustrating the fibre cloth inspecting method of the one embodiment according to the present invention.

Refer to FIG. 1. FIG. 1 is a flowchart illustrating the fibre cloth inspecting method of the one embodiment according to the present invention. And also Refer to FIG. 2-FIG. 6 with FIG. 1.

The fibre cloth inspecting method are provided for inspecting a fibre cloth 1 regarding sparse density, filament break, various kinds of mark, fabric runs, break, weaving validation, and dyeing uniformity. The fibre cloth inspecting method can be applied to an inspecting system. The inspecting system includes an optical scanning means 2. The optical scanning means 2 includes a light source body 21, a light transmissive member 22, and a light sensitive member 23. The fibre cloth inspecting method comprises following steps: scanning the fibre cloth by a scanning light beam (Step S10); retrieving a light pattern generated by the scanning (Step S20); generating an inspecting result information according to the light pattern in relation to the fibre cloth (Step S30); and analyzing the fibre cloth regarding sparse density, filament break, various kinds of mark, fabric runs, break, weaving validation, and dyeing uniformity according to the inspecting result information (Step S40).

In order to clearly realize the condition of the sparse density, the filament break, the various kinds of mark, the fabric runs, the break, the weaving validation, and the degree of dyeing uniformity, in a preferred embodiment, after step S40, it further comprises steps of: determining the fibre cloth as a defective product while the quality of fibre cloth including sparse density, filament break, the various kinds of mark, fabric runs, break, weaving validation, and dyeing uniformity exceeds a predetermined level (Step S50); processing the inspecting result information to obtain an inspecting map (Step S60); marking a problem area on the inspecting map according to the quality of fibre cloth including sparse density, filament break, various kinds of mark, fabric runs, break, weaving validation, and the dyeing uniformity of the fibre cloth (Step S70).

Figure 2:
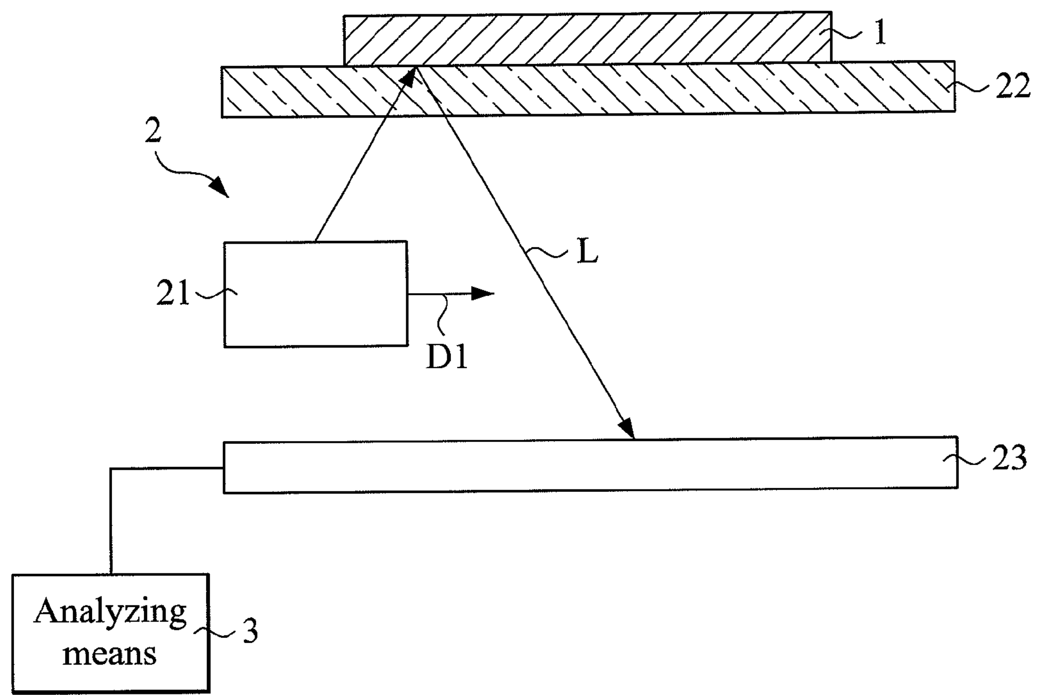
FIG. 2 is a schematic diagram illustrating an inspecting system performing the fibre cloth inspecting method of the one embodiment according to the present invention.
Figure 3:
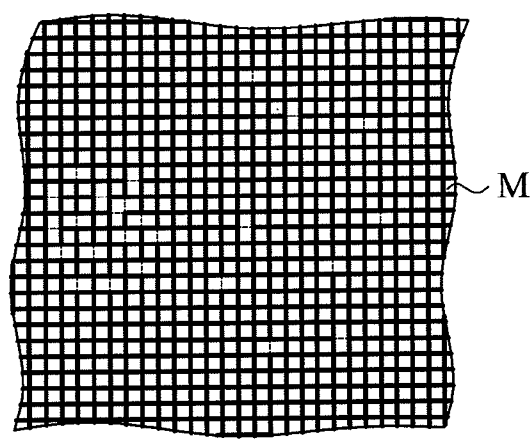
FIG. 3 is a schematic diagram illustrating one inspecting map of the one embodiment according to the present invention.
Figure 4:
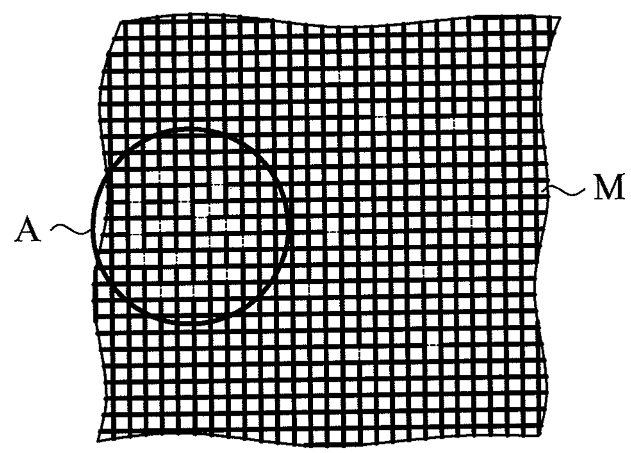
FIG. 4 is a schematic diagram illustrating another one inspecting map of the one embodiment according to the present invention.
Figure 5:
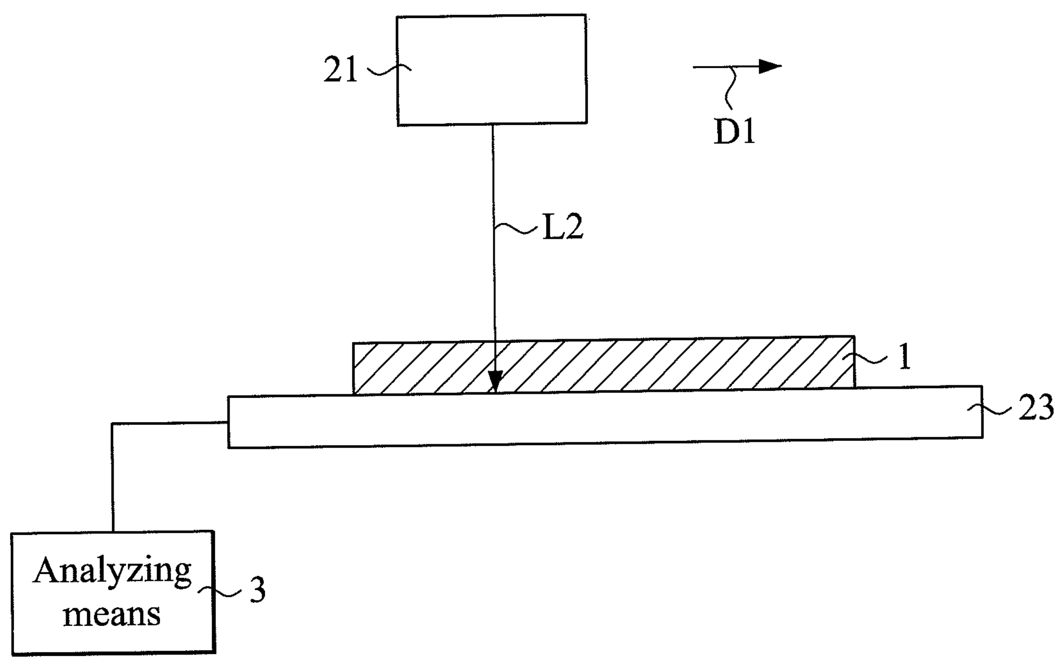
FIG. 5 is a schematic diagram illustrating an inspecting system performing the fibre cloth inspecting method of the another one embodiment according to the present invention.
Figure 6:
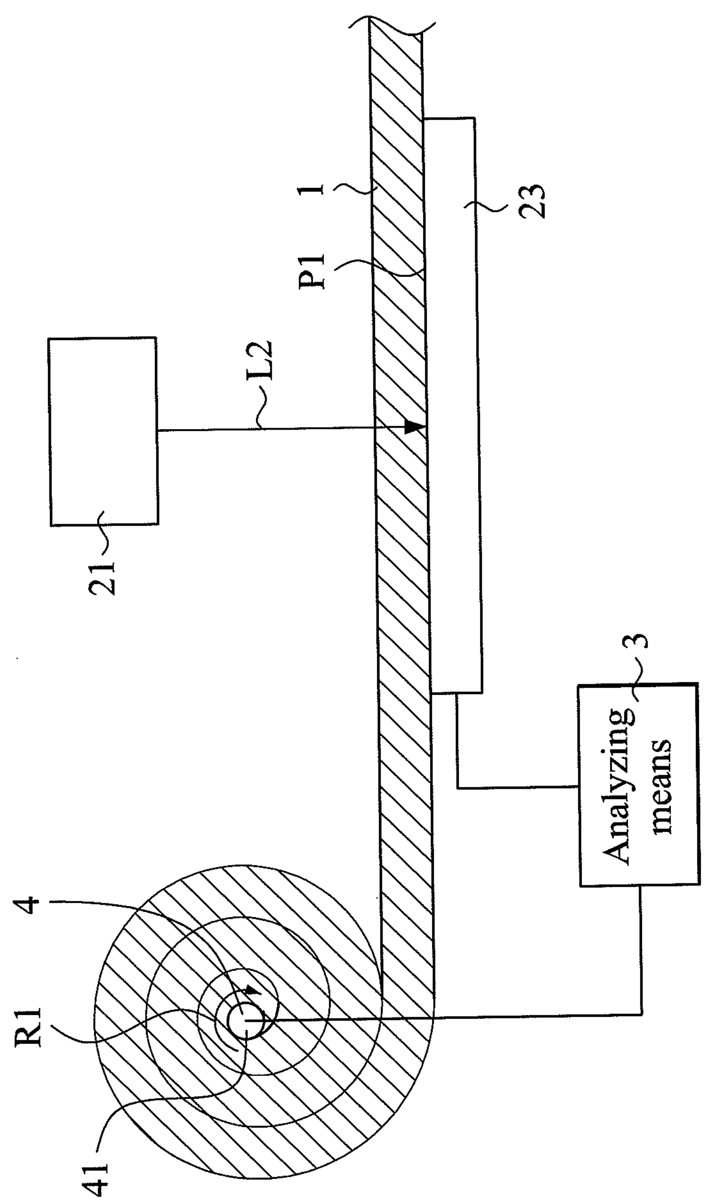
FIG. 6 is a schematic diagram illustrating an inspecting system performing the fibre cloth inspecting method of the another one embodiment according to the present invention.

The fibre cloth 1 is disposed on the light transmissive member 22, as shown in FIG. 2. First, scan the fibre cloth with a scanning light beam L projecting from the light source body 21 (Step S10). In the embodiment, the light source body 21 moves along a length direction D1 of the fibre cloth 1, so that the scanning light beam L can scan all length of the fibre cloth 1. Since the light transmissive member 22 allows the light to pass through, the scanning light beam L can pass through the light transmissive member 22 to scan fibre cloth 1. In the Step S10, a light pattern is generated by having the scanning light beam L reflecting from the fibre cloth 1, and the light pattern passes through the light transmissive member 22 to project on the light sensitive member 23. In addition, in other embodiments, the fibre cloth 1 can be directly disposed on the light sensitive member 23, and the light pattern is generated by having light source body 21 passing through the fibre cloth 1 is projecting toward the scanning light beam L2 (as shown in FIG. 5 and FIG. 6). Moreover, in the situation that the length of the fibre cloth 1 is longer than that of the light sensitive member 23, in order to inspect all length of the fibre cloth 1 regarding the sparse density, the filament break, the various kinds of mark, the fabric runs, the break, the weaving validation, and the dyeing uniformity, the fibre cloth 1 is shifted to move along a guiding path P1 to pass through a projecting area projected by the scanning light beam projecting from the light source body 21 (as shown in FIG. 6). A pulling means 4 pulls the fibre cloth along the guiding path P1 (the direction of the guiding path P1 is contrary to that of the length direction D1 in FIG. 2) to make the fibre cloth 1 move to pass through a protecting area projected by the scanning light beam L2 projecting from the light source body 21. The pulling means 4 has a scroll 41 that rotates in a rotation direction R1 to pull the fibre cloth 1 and to scroll one end of the fibre cloth 1. By means of the pulling means 4, the light source body 21 and the fibre cloth 1 move relatively to each other, so that the position of the light source body 21 can be fixed and that the light source body 21 does not have to move along the length direction of the fibre cloth as shown in FIG. 2 and FIG. 5.

Figure 7:
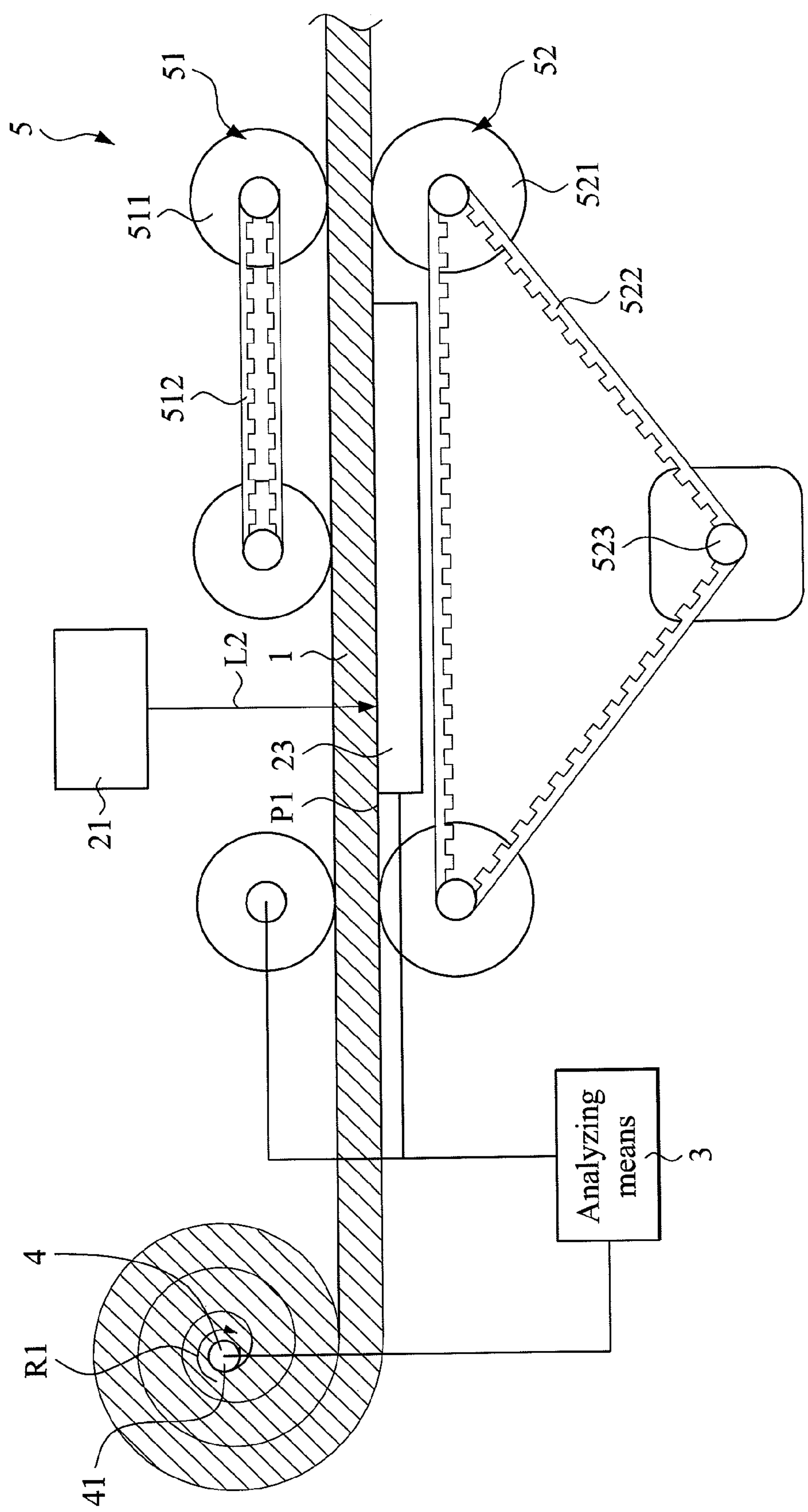
FIG. 7 is a schematic diagram illustrating an inspecting system performing the fibre cloth inspecting method of the another one embodiment according to the present invention.
Figure 8:
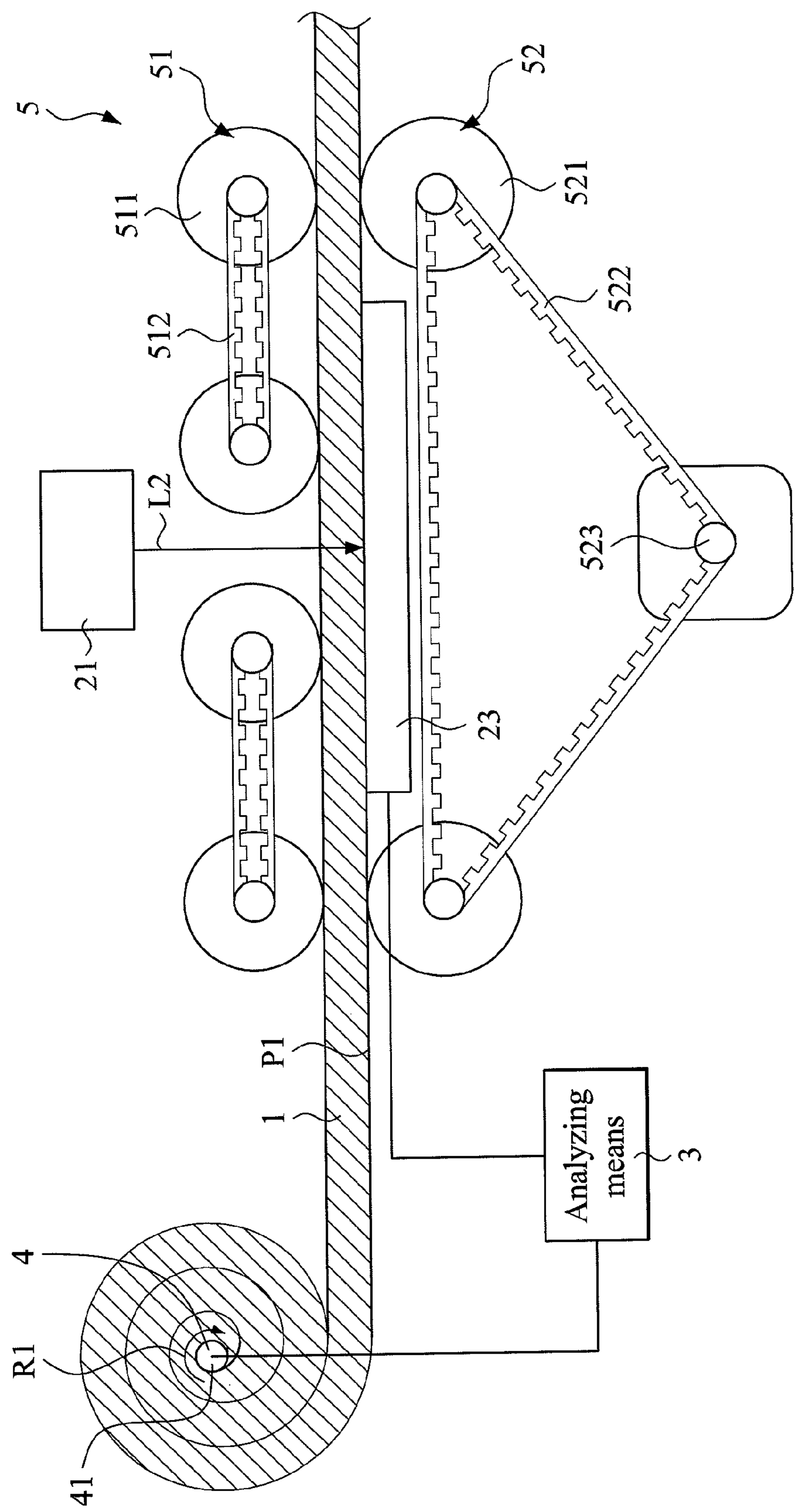
FIG. 8 is a schematic diagram illustrating an inspecting system performing the fibre cloth inspecting method of the another one embodiment according to the present invention.

In order to prevent the fibre cloth 1 from being wrinkled during being pulled, in other embodiments, a pressing guiding means 5 is provided to press and to guide the fibre cloth 1 simultaneously as shown in FIG. 7 and FIG. 8). The pressing guiding means 5 includes an upper guiding member 51 and a lower guiding member 52. The upper guiding member 51 includes a roller member 511 contacting the upper surface of the fibre cloth 1. The lower guiding member 52 includes a roller member 521 contacting the lower surface of the fibre cloth 1. And the upper guiding member 51 and the lower guiding member 52 that both at the same position of the fibre cloth 1 press each other and rotate in different directions, thereby the fibre cloth 1 is smoothly pressed and guided. In addition, the upper guiding member 51 further includes a transmitting member 512 connecting a plurality of roller members 511, and the lower guiding member 52 further includes a transmitting member 522 connecting a plurality of roller members 521. The transmitting member 512, 522 may be a chain, a belt, or the like. The lower guiding member 52 further includes a driving member 523 driving the roller member 521 by transmitting the power through the transmitting member 522. Thereby the members of the pressing guiding means 5 can guide the fibre cloth 1 synchronously and press a length of the fibre cloth 1 reliably.

Meanwhile, light sensitive member 23 retrieves a light pattern generated by scanning the fibre cloth 1 (Step S20). The light pattern is transmitted to an analyzing means 3 connecting with the light sensitive member 23, so that the light sensitive member 23 generates an inspecting result information according to the light pattern in relation to the fibre cloth 1 (Step S30). A positional mapping relation between the light pattern and the fibre cloth 1 is determined according to the position of the scanning light beam L projecting on the light sensitive member 23. In the FIG. 6, a positional mapping relation between the light pattern and the fibre cloth 1 is determined according to the position of the fibre cloth 1 relative to the guiding path P1. And the position of the fibre cloth 1 relative to the guiding path P1 can be determined according to a pulling speed of the pulling means 4 (i.e. the value that the angular velocity of the scroll 41 times the radius of the scroll 41 in this embodiment).

Then, the analyzing means 3 analyzes the fibre cloth 1 regarding the sparse density, the filament break, the various kinds of mark, the fabric runs, the break, the weaving validation, and the dyeing uniformity according to the inspecting result information (Step S40), wherein the sparse density, the filament break, the various kinds of mark, the fabric runs, the break, the weaving validation, and the dyeing uniformity of the fibre cloth 1 is analyzed by the analyzing means 3 according to the magnitude and the color level of the light pattern. And the position, the quantity, and the size of those also can be obtained.

Furthermore, after Step S40, in the embodiment, a predetermined level is set in the analyzing means 3. The analyzing means 3 determines the fibre cloth 1 as a defective product while a quality of fibre cloth regarding sparse density, filament break, various kinds of mark, fabric runs, break, weaving validation, and dyeing uniformity of the fibre cloth 1 exceeds the predetermined level (Step S50). For example, the quantity of the filament break exceeds 10, or the total area of the filament break exceeds 1 $cm^2$. Moreover, the analyzing means 3 further can processes the inspecting result information to obtain an inspecting map M that provides an obvious image for observing the sparse density, the filament break, the various kinds of mark, the fabric runs, the break, the weaving validation, and the dyeing uniformity, as show in FIG. 3 (Step S60). In addition, the analyzing means 3 marks a problem area A on the inspecting map M according to quality of fibre cloth regarding sparse density, filament break, the various kinds of mark, the fabric runs, the break, the weaving validation, and the dyeing uniformity (Step S70). By means of the assistance, the severe problem area regarding the sparse density, the filament break, the various kinds of mark, the fabric runs, the break, the weaving validation, and the dyeing uniformity can be observed more directly.

The above description should be considered as only the discussion of the preferred embodiments of the present invention. However, a person skilled in the art may make various modifications to the present invention. Those modifications still fall within the spirit and scope defined by the appended claims.

What is claimed is:

1. A fibre cloth inspecting method for inspecting a fibre cloth regarding sparse density, filament break, various kinds of mark, fabric runs, break, weaving validation, and dyeing uniformity, comprising steps of:

(a) scanning the fibre cloth, which is disposed on a light transmissive member, by projecting a scanning light beam through the light transmissive member to the fibre cloth and then receiving, by a light sensitive member, the scanning light beam reflected from the fibre cloth through the light transmissive member;

(b) retrieving a light pattern formed on the light sensitive member, wherein the light pattern is generated by receiving the scanning light beam reflected from the fibre cloth;

(c) generating an inspecting result information according to the light pattern in relation to the fibre cloth;

(d) analyzing the fibre cloth regarding sparse density, filament break, various kinds of mark, fabric runs, break, weaving validation, and dyeing uniformity according to the inspecting result information;

(e) processsing the inspecting result information to obtain an inspecting map; and (f) marking a problem area on the inspecting map according to a quality of fibre cloth regarding sparse density, filament break, various kinds of mark, fabric runs, break weaving validation, and dyeing uniformity of the fibre cloth.

2. The fibre cloth inspecting method as claimed in claim 1, wherein in the step (a), the fibre cloth is shifted along a guiding path to pass through a projecting area projected by the scanning light beam.

3. The fibre cloth inspecting method as claimed in claim 2, wherein in the step (c), a positional mapping relation between the light pattern and the fibre cloth is determined according to the position of the fibre cloth relative to the guiding path.

4. The fibre cloth inspecting method as claimed in claim 1, wherein in the step (d), the sparse density, the filament break, the various kinds of mark, the fabric runs, the break, the weaving validation, and the dyeing uniformity of the fibre cloth is analyzed according to the magnitude and the color level of the light pattern.

5. The fibre cloth inspecting method as claimed in claim 1, further comprising, after step (d), a step of determining the fibre cloth as a defective product while a quality of fibre cloth regarding sparse density, filament break, various kinds of mark, fabric runs, break, weaving validation, and dyeing uniformity of the fibre cloth exceeds a predetermined level.

6. The fibre cloth inspecting method as claimed in claim 1, wherein in the step (a), the fibre cloth is guided and pulled by a pulling means to pass through a projecting area projected by the scanning light beam, and in the step (c), a positional mapping relation between the light pattern and the fibre cloth is determined according to a pulling speed of the pulling means.

* * * * *